United States Patent [19]

Georgalas et al.

[11] Patent Number: 4,603,046
[45] Date of Patent: Jul. 29, 1986

[54] IMPROVED SUNSCREEN OR SUNBLOCK COMPOSITION

[75] Inventors: Arthur C. W. Georgalas, Leonardo; George E. Deckner, Westfield, both of N.J.

[73] Assignee: Charles of the Ritz Group Ltd., New York, N.Y.

[21] Appl. No.: 768,586

[22] Filed: Aug. 23, 1985

[51] Int. Cl.[4] ............................ A61K 7/42; A61K 7/44
[52] U.S. Cl. ........................................ 424/59; 424/60; 514/847; 536/8
[58] Field of Search ...................... 424/59, 60; 536/8; 514/847

[56] References Cited

U.S. PATENT DOCUMENTS 2,646,428 7/1953 Chabrier et al. ...................... 536/8
2,890,225 6/1959 Gregory ............................ 424/59 X
2,975,168 3/1961 Favre ................................. 536/8
4,153,788 5/1979 Courbat et al. ...................... 536/8

FOREIGN PATENT DOCUMENTS 856150 7/1949 Fed. Rep. of Germany .......... 536/8

OTHER PUBLICATIONS

"Zeitschrift fuer Haut und Geschlechtskrankheiten", No. 21, 224 (1956), The Effects of Ultraviolet Radiation on the Human Skin, Report No. 6: Experiments with Topical Substances of the Vitamin B–Group, by H. Tronnier and H. Linnenkohl.
"The Merck Index", Tenth Edition, paragraph 9590, Troxerutin.

Primary Examiner—Dale R. Ore
Attorney, Agent, or Firm—Lawrence S. Levinson; Burton Rodney

[57] ABSTRACT

Skin treatment compositions such as sunscreen compositions and moisturizer compositions are provided which include a tri(hydroxyalkyl)rutoside as a UV-A absorber and moisturizer, such as troxerutin preferably in combination with 4-(dimethylamino)benzoic acid, 2-ethylhexyl ester.

18 Claims, No Drawings

IMPROVED SUNSCREEN OR SUNBLOCK COMPOSITION

FIELD OF THE INVENTION

The present invention relates to improved skin treatment compositions, such as sunscreen compositions and moisturizer compositions.

BACKGROUND OF THE INVENTION

Ultraviolet energy absorbed by the human skin can produce an erythemal reaction (redness), the intensity of which is dependent upon the amount of energy absorbed. Ultraviolet radiation from both sunlight and artificial sources has been divided into three bands (UV-A, UV-B, and UV-C) which emit different quantities of energy and therefore produce an erythemal reaction at different time intervals after exposure. The amount of energy from any source required to produce to minimally perceptible redness reaction of the skin is termed the Minimal Erythema Dose or MED.

UV-A radiation is present in the sunlight reaching the earth's surface and has a wavelength of 320 to 400 nanometers (nm.). It can cause tanning of the skin but is weak in causing reddening of the skin. About 20 to about 50 joules/cm$^2$ of UV-A energy is required to produce one MED. The erythema reaction is maximal in intensity about 24 hours after exposure.

UV-B radiation is present in the sunlight reaching the earth's surface and has a wavelength of 290 of 320 nm. It causes the sunburn reaction which also stimulates pigmentation (tanning) in the skin. Approximately 20 to 50 millijoules/cm$^2$ of UV-B energy is required to produce one MED (i.e., about 1,000 times less than the dose of UV-A). The erythema reaction is maximal in intensity at from about 6 to about 20 hours after exposure.

UV-C radiation has a wavelength of 200 to 290 nm. and is not present in the sunlight reaching the earth's surface but can be emitted by artificial ultraviolet sources. It is not effective in stimulating pigmentation but does cause erythema requiring about 5 to 20 millijoules/cm$^2$ to produce one MED.

The tanning ability of an individual is genetically predetermined and is governed by the individual's capacity to produce melanin pigment within the pigment cells when stimulated by UV-B and UV-A. The extent of any erythemal response is a function of skin color and thus less time is required to produce a MED in light skinned individuals than to produce a MED in dark skinned individuals.

The most rapid way to cause tanning is to allow the sun to produce erythema of the skin. Erythema sufficient to induce tanning yet not so severe as to cause pain requires only half the time of exposure that is required to produce a painful sunburn. Suntanning can occur at the UV-A wavelengths but develops slowly under natural conditions. Tanning most commonly develops after exposure to the "sunburn" UV-B band.

Sunscreen preparations are commercially available which extend the time it takes the sun to produce a sunburn. Such preparations contain chemicals which can absorb ultraviolet light at various wavelengths, for example, 4-(dimethylamino)benzoic acid, 2-ethylhexyl ester (Escalol 507) and 2-hydroxy-4-methoxybenzophenone (UVinul M40) which absorb UV-A, or an opaque substance that physically reflects or scatters the ultraviolet light, i.e. talc.

Ultraviolet absorbing compounds and sunscreen compositions containing the same are disclosed, for example, in U.S. Pat. Nos. 3,004,896; 3,189,615; 3,403,207; 3,479,428; 3,644,614; 3,670,074; 3,751,563; 3,821,363; 3,892,844; 4,514,383; and British Pat. No. 1,291,917.

SUMMARY OF THE INVENTION

This invention is directed to improved skin treatment compositions such as sunscreen formulations having enhanced ultraviolet absorbing properties and improved moisturizer compositions. The skin treatment composition is preferably an oil-in-water emulsion which contains water, emollients, emulsifiers, preservatives, antioxidants, and optionally one or more known ultraviolet absorbing compounds. The ultraviolet absorbing property and/or moisturizing property of the composition is enhanced by including from about 0.2% to about 5% by weight of a tri(hydroxyalkyl)rutoside preferably troxerutin, and preferably from about 0.3% to about 3.0% by weight of troxerutin.

DESCRIPTION OF THE INVENTION

In accordance with the present invention, skin treatment compositions, such as sunscreen and sunblock formulations, and moisturizer formulations are provided, which compositions have improved moisturizer ability and sunscreen properties due to the presence therein of a tri(hydroxyalkyl)rutoside, preferably troxerutin, which is especially effective in absorbing UV-A radiation, and are preferably in the form of an oil-in-water emulsions which contain water, emmolients, emulsifiers, thickeners, preservatives, coloring agents, fragrances, antioxidants and the like, and preferably one or more known ultraviolet absorbing compounds (in the case of sunscreen or sunblock formulations). In fact, the moisturizer compositions of the invention will be similar in composition to the sunscreen or sunblock formulations and may or may not include the optional ultraviolet absorbing compound.

In addition, in accordance with the present invention, a unique combination of ultraviolet absorbers is provided comprising troxerutin and 4-(dimethylamino)benzoic acid, 2-ethylhexyl ester.

As will be seen hereinafter, it has surprisingly been found that the preferred combination of troxerutin and 4-(dimethylamino)benzoic acid, 2-ethylhexyl ester when employed in a sunscreen and/or sunblock composition, in accordance with the present invention, is a synergistic combination in that the combined sunscreen effect of the two components is surprisingly superior to the sunscreen effect of either of the components taken alone.

In formulating compositions containing the synergistic combination, the troxerutin should be employed in a weight ratio to the 4-(dimethylamino)benzoic acid, 2-ethylhexyl ester of within the range of from about 0.04:1 to about 3:1, and preferably from about 0.1:1 to about 2:1.

The formulation of the invention is preferably an oil-in-water type emulsion since this type of emulsion affords better cosmetic feel to the product. However, the product could also be formulated as a water-in-oil emulsion, cream base, or oil base. Depending upon the choice of ingredients, the formulation has a semi-solid cream-like consistency which can be packaged in a plastic squeeze tube or it has a lotion type consistency which can be packaged in a plastic squeeze container.

The container can include a flow-type cap or pump-type dispenser.

The essence of the present invention resides in the use of a tri(hydroxyalkyl)rutoside, preferably troxerutin, to impart good moisturizing properties and to enhance sunscreening properties of other sunscreen agents or sunblock agents which are present. Thus, the composition of the invention, regardless of whether it is a sunscreen, sunblock, moisturizer, etc. will contain from about 0.2 to about 5% and preferably about 0.3 to about 3% by weight (based on the total weight of the formulation) of tri(hydroxyalkyl)rutoside. Where amounts less than 0.2% tri(hydroxyalkyl)rutoside are employed, the moisturizing properties and sunscreen properties imparted will be minimal and unacceptable, whereas, where amounts greater than 5% by weight are employed, increase in moisturizing and sunscreen properties imparted will be minimal and unwarranted considering the expense of raw materials involved.

The tri(hydroxyalkyl)rutoside compounds employed in the present invention will have the formula

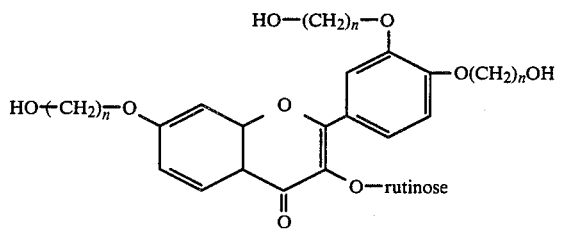

wherein n is 1 to 4 and preferably 2, so that the compound is troxerutin, that is tri(hydroxyethyl)rutin. These compounds are commercially available and/or may be prepared by conventional techniques.

Other examples of tri(hydroxyalkyl)rutoside compounds suitable for use herein include but are not limited to tri(hydroxymethyl)rutoside, tri(hydroxypropyl)rutoside and tri(hydroxybutyl)rutoside, all of which may be prepared employing conventional procedures.

Where the formulation is a sunscreen or sunblock formulation, it will contain, in addition to the tri(hydroxyalkyl)rutinoside which absorbs ultraviolet in the UV-A region, one or more known ultraviolet absorbing agents, preferably at least one compound which absorbs in the UV-B region (wavelength 290 to 320 nanometers) and optionally one or more other compounds which absorb in the UV-a region (wavelength 320 to 400 nanometers). The total amount of UV absorbing agents included within the formulation will be from about 2% to about 15% by weight, which amount will determine whether it is a sunscreen or sunblock.

Suitable UV-A absorbing agents which may be employed in addition to the tri(hydroxyalkyl)rutoside include 2-(2'-hydroxy-5'-methylphenyl)benzotriazole (Tinuvin P); 2-(2'-hydroxy-5'-t-octylphenyl)benzotriazole (Spectra-Sorb UV 5411); 2,4-dihydroxybenzophenone (Uvinul 400); 2-hydroxy-4-methoxybenzophenone (oxybenzone, Spectra-Sorb UV9, Uvinul M-40); 2,2', 4,4'-tetrahydroxybenzophenone (Uvinul D50); 2,2'-dihydroxy-4,4'-dimethoxybenzophenone (Uvinul D49); 2,2'-dihydroxy-4-methoxybenzophenone (dioxybenzone, Spectra-Sorb UV24); 2-ethylhexyl-4-phenyl-benzophenone carbonate (Eusolex 3573); 2-hydroxy-4-methoxy-4'-methylbenzophenone (mexenone, Uvistat 2211); 2-hydroxy-4-(n-octyloxy)benzophenone (octabenzone, Spectra-Sorb UV531); 4-phenylbenzophenone (Eusolex 3490); and 2-ethylhexyl-2-cyano-3,3'-diphenylacrylate (Uvinul N539); butyl methoxydibenzoyl methane (Parsol 1789), and benzphthalide (Escalol 547). The UV-A absorbing agent or agents are present in the final product at from 0 to about 10% by weight of the formulation. The amount will vary according to the particular agent selected and whether the formulation is intended to minimize or permit tanning. Where a UV-A absorbing agent is employed, the preferred UV-A absorbing agent is 2-hydroxy-4-methyoxybenzophenone alone or in combination with 2,2'-dihydroxy-4-methoxybenzophenone.

Suitable UV-B absorbing agents include 4-(dimethylamino)benzoic acid, ethyl ester; 4-(dimethylamino)benzoic acid, 2-ethylhexyl ester (Escalol 507); 4-(dimethylamino)benzoic acid, pentyl ester (Escalol 506); glyceryl p-aminobenzoate (Excalol 106); isobutyl p-aminobenzoate (Cycloform); and isopropyl p-aminobenzoate; 2-ethylhexyl methoxy cinnamate (Parsol MCX); phenylbenzimidazole sulfonic acid (Eusolex 232); homomenthyl salicylate, and ethyl hexyl salicylate. The UV-B absorbing agent or agents are present in the final product at from about 1% to about 15% by weight of the formulation. The amount will vary according to the particular agent selected and degree of protection desired in the final product. The preferred UV-B absorbing agent is 4-(dimethylamino)benzoic acid, 2-ethylhexyl ester (Escalol 507).

The formulation also contains from about 50% to about 90% and preferably from about 60 to about 80% by weight of water, from about 1% to about 20% and preferably from about 1 to about 5% by weight of emollients, from about 1% to about 10% and preferably from about 1 to about 5% by weight of emulsifiers, from about 0.05 to about 2% and preferably from about 0.1 to about 1% by weight of preservatives and antioxidants, and less than about 1% by weight of fragrance and coloring agents.

Suitable emollients include mineral oil, avocado oil, squalane, octyl palmitate, cocoa butter, sesame oil, petrolatum, propylene glycol dicaprylate/dicaprate, isopropyl myristate, etc. The formulation will preferably contain a mixture of several of these emollients or others which are approved for cosmetic use.

Suitable emulsifiers include polyethylene glycol 20 sorbitan monolaurate (Polysorbate 20), diethanolamine cetyl phosphate, glyceryl stearate, polyethylene glycol 100 stearate, polyethylene glycol 20 stearyl ether (Brij 78, Steareth 20), polysorbate 80 (Tween 80), etc. The formulation will preferably contain a mixture of two or more of these emulsifiers or others which are approved for cosmetic use.

Suitable preservatives include imidazolidinyl urea (Germall 115), methylparaben (Tegosept M), quaternium-15 (N-(3-chloroallyl)hexaminium chloride, Dowicil 200), propylparaben (Tegosept P), dimethyldimethoyl hydantoin, benzyl alcohol and/or phenoxyethanol, etc., and a preferred antioxidant is a mixture of butylated hydroxyanisole, propylene glycol, propyl gallate and citric acid (Tenox 2). The formulation will preferably contain the antioxidant mixture and one or more of the preservatives or any other preservatives and antioxidants approved for cosmetic use.

As discussed above, by varying the percentage of ingredients the fomulation can be obtained in a lotion or semi-solid form. For example, in formulating the product as a lotion, water would be included at from about 60% to 65% by weight of the final product and one or more humectants such as propylene glycol, glycerin, 1,3-butylene glycol, sorbitol, polyethylene glycols (for example, Carbowax 400), could be included at up to about 7.5% by weight of the final product.

The composition of the invention will optionally include a thickener in an amount within the range of from about 0.05 to about 1% and preferably from about 0.05 to about 0.3% by weight. A preferred thickener suitable for use herein is Carbopol 940 or Carbomer 940 which is hydrophilic acrylic polymer cross-linked with a polyfunctional agent and employed with an organic or inorganic base, preferably triethanolamine. Other examples of thickeners which may be employed herein include, but are not limited to, stearic acid, magnesium aluminum silicate, stearoxydimethicone, hydroxyethyl cellulose, hydroxypropyl cellulose or xanthan gum.

Skin conditioning agents which may optionally be present in the composition of the invention include allantoin, d- or dl-panthenol, hydrolyzed animal protein and the like. Such conditioning agents may be present in an amount within the range of from about 0.01 to about 5% and preferably from about 0.05 to about 2% by weight and optimally from about 0.1 to about 2% by weight depending upon the ultimate use of the skin preparation.

The process techniques will vary depending upon the particular ingredients present. In a preferred process, one or more thickeners such as stearic acid, one or more emulsifiers, emollient, such as dimethicone (Silicon 225), preservative, such as propyl paraben, Escalol 507 and/or other sunscreen agents (where present) are blended together with moderate mixing to form a first non-aqueous blend. A second blend of deionized water, gum thickener, such as Carbopol 940 and other water-soluble ingredients, if desired, and a third blend of humectant, for example, a polyethylene glycol (such as Carbowax 400) and preservative, such as methyl paraben and benzyl alcohol are formed. The first non-aqueous blend is sweep mixed into the second and third blends to form an emulsion. Thereafter, a blend of a small amount of deionized water and troxerutin or other tri(hydroxyalkyl)rutoside and other water-soluble ingredients which can be included with this aqueous phase is added to the emulsion with mixing. Thereafter, the final blend is cooled to room temperature, homogenized, stored or packaged.

Preferred sunblock formulations offering maximum protection according to this invention include from about 60% to about 80% by weight of water, from about 0.3% to about 3% by weight of troxerutin and optionally from about 2.5% to about 3.5% by weight of other UV-A absorbing agents selected from 2-hydroxy-4-methoxybenzophenone (oxybenzone) and 2,2'-dihydroxy-4-methoxybenzophenone (dioxybenzone), and preferably from about 2% to about 10% by weight of the UV-B absorbing agent 4-(dimethylamino)benzoic acid, 2-ethylhexyl ester (Escalol 507), from about 1 to about 5% by weight of humectants, from about 1% to about 5% by weight of emollients, from about 1% to about 5% by weight of emulsifiers, from about 0.1 to about 0.5% by weight thickeners, and up to about 1% by weight of combined preservatives, antioxidants, and fragrances.

Most preferably the maximum protection formulation will contain about 73% by weight of deionized water, about 1% by weight of troxerutin, and optionally about 3% by weight of 2-hydroxy-4-methoxybenzophenone, up to about 1% by weight of 2,2'-dihydroxy-4-methoxybenzophenone, about 4% by weight of 4-(dimethylamino)benzoic acid, 2-ethylhexyl ester, about 3% by weight of emollients, about 5% by weight of emulsifiers, about 0.35% by weight thickener, and up to about 1% by weight of combined preservatives, antioxidants, and fragrances.

Preferred sunscreen formulations which protect but still permit gradual tanning according to this invention contain from about 55% to about 65% by weight of water, from about 0.5 to about 1% by weight of troxerutin, up to about 1% by weight of 2-hydroxy-4-methoxybenzophenone (oxybenzone), from about 3% to about 5% by weight of 4-(dimethylamino)benzoic acid, 2-ethylhexyl ester (Escalol 507), up to about 7.5% by weight of humectants, from about 1 to about 5% by weight of emollients, from about 1% to about 10% by weight of emulsifiers, and up to about 1% by weight of combined preservatives, antioxidants, and fragrances.

The most preferred sunscreen formulation which still permits tanning is a lotion containing from about 60% to about 61% by weight of deionized water, about 1% by weight of troxerutin, about 0.6% by weight of 2-hydroxy-4-methoxybenzophenone, about 4% by weight of 4-(dimethylamino)benzoic acid, 2-ethylhexyl ester, about 5% by weight of glycerin or propylene glycol, about 2% to about 4% by weight of emollients, from about 3% to about 8% by weight of emulsifiers, and up to about 1% by weight of combined preservatives, anitoxidants and fragrances.

Preferred moisturizer compositions will be similar to the sunscreen and sun block formulations set out above without the sunscreen agents.

The following Examples represent preferred embodiments of the invention. Unless otherwise indicated, all temperatures are expressed in degrees Centigrade.

EXAMPLES 1 TO 3

Sunscreen oil-in-water formulations in the form of lotions having the following compositions were prepared as described below.

| Ingredient | Parts by Weight Example No. | | |
|---|---|---|---|
| | 1 | 2 | 3 |
| Blend I | | | |
| Deionized water | 68.3 | 68.3 | 68.3 |
| Magnesium aluminum silicate (Veegum R, thickener) | 0.5 | 0.5 | 0.5 |
| Blend II | | | |
| Polyethylene glycol 400 (humectant) | 5 | 5 | 5 |
| Methyl paraben (Tegosept M, preservative) | 0.2 | 0.2 | 0.2 |
| Xanthan gum (Keltol F, thickener) | 0.2 | 0.2 | 0.2 |
| Blend III | | | |
| Polyethylene glycol stearyl ether (Brij 78, emulsifier) | 1 | 1 | 1 |
| Cetyl alcohol (thickener, emollient) | 0.5 | 0.5 | 0.5 |
| Stearic acid (thickener) | 2 | 2 | 2 |
| Propylparaben (Tegosept P, preservative) | 0.1 | 0.1 | 0.1 |
| Butylparaben (Tegosept B, preservative) | 0.1 | 0.1 | 0.1 |
| Polyethylene glycol 100 stearate and glycerol monostearate (1:1) (Arlacel 165, emulsifier) | 2 | 2 | 2 |
| $C_{12}$-$C_{15}$ alcohol benzoate (Finsolv TN, emollient) | 4 | 2 | 1 |
| Polyethylene glycol 5 soya | 0.5 | 0.5 | 0.5 |

-continued

| Ingredient | Parts by Weight Example No. | | |
|---|---|---|---|
| | 1 | 2 | 3 |
| sterol (Generol 122 E5, emollient, emulsifier) | | | |
| Cetearyl octanoate (Purcellin oil, emollient) | 4 | 4 | 3 |
| 4-(Dimethylamino)benzoic acid, 2-ethylhexyl ester (Escalol 507, sunscreen, UV-B) | 0 | 2 | 4 |
| Blend IV | | | |
| Deionized water | 10 | 10 | 10 |
| Troxerutin (tri(hydroxyethyl)rutoside) (sun protection | 1 | 1 | 1 |
| Blend V | | | |
| Chloroallyl methenamine chloride (Dowicil 200, preservative) | 0.1 | 0.1 | 0.1 |
| Deionized water | 0.5 | 0.5 | 0.5 |

Aqueous Blend I was prepared by mixing the thickener ingredients in the deionized water. Blend II, prepared by simple mixing of ingredients, was then mixed with Blend I. The combined Blends I-II was then heated to 75° C.

Blend III was formed by simple mixing of the ingredients in a separate vessel while heating at 75° C.

Blend III (heated at 75° C.) was then added to the combined Blend I-II (also at 75° C.) with sweep mixing.

The combined Blend I-II-III was heated at 75° C. for 30 minutes, allowed to air cool to 60° C. and then Blends IV and V each formed by simple mixing of ingredients were separately added with sweep mixing.

The resulting batch was then allowed to air cool to 30° C. to form the sunscreen formulations of the invention.

As Controls, two additional formulations were prepared, namely Control A, which was the same as Example 1 except that it did not contain troxerutin or Escalol 507 or any other sunscreen agent, and is referred to as the "base formulation", and Control B which was the same as the Example 3 formulation except that it did not contain any troxerutin and only contained 4% Escalol 507.

The above sunscreen formulations of Examples 1, 2 and 3 and Controls A and B were subjected to sun protection factor (SPF) testing. SPF value was determined by dividing minimal erythema dose (MED) for protected skin after the application of 2 mg/cm$^2$ of the formulation by the MED for unprotected skin.

SPF values for the above formulations were found to be as follows:

| Example No. | | SPF Value |
|---|---|---|
| 1. | (1% troxerutin and no Escalol 507) | 2.4 |
| 2. | (1% troxerutin and 2% Escalol 507) | 5.9 |
| 3. | (1% troxerutin and 4% Escalol 507) | 8.1 |
| 4. | Control A (base) (0% troxerutin, 0% Escalol 507) | 2 |
| 5. | Control B (0% troxerutin and 4% Escalol 507) | 5.5 |

The above results clearly showed that the Example 3 formulation which contains a combination of 1% troxerutin and 4% Escalol 507 and has an SPF value of 8.1 is surprisingly far and away superior to the Control B formulation which contains no troxerutin and 4% Escalol 507 and has an SPF value of 5.5; thus the Example 3 formulation has about a 32% increase in sun protection over the Control B formulation and over a 400% increase in sun protection over the Control A base formula.

This is especially surprising inasmuch as the Example 1 formulation which contained 1% troxerutin and no Escalol 507 had an SPF value of 2.4 or only about a 20% increase over the base formulation (Control A).

EXAMPLES 4 AND 5

Moisturizer formulation having the following compositions were prepared as described below. The ingredients are listed on parts by weight basis and both the CTFA and trade name are included. The formulations are an oil-in-water type emulsion and are in the form of lotions.

| Ingredient | Parts by Weight Example No. | |
|---|---|---|
| | 4 | 5 |
| Blend I | | |
| Deionized water | 39.8 | 39.9 |
| Magnesium aluminum silicate (Veegum R, thickener) | 1.2 | 1.2 |
| TiO$_2$ (color) | 0.2 | 0.2 |
| Umber 2736 (color) | 0.04 | 0.04 |
| Yellow 2576 (color) | 0.2 | 0.15 |
| Blend II | | |
| Glycerine (humectant) | 5 | 5 |
| Polyethylene glycol 400 (humectant) | 2 | 2 |
| Methylparaben (Tegosept M, preservative) | 0.25 | 0.25 |
| Blend III | | |
| Ozokerite (hydrocarbon wax, emollient) | 2 | 2 |
| Hydrogenated lanolin (Satulan, emollient) | 1 | 1 |
| Squalene (Robane, emollient) | 0.1 | 0.1 |
| Propylparaben (Tegosept P, preservative) | | |
| Stearic acid (thickener) | 5 | 5 |
| Butylated hydroxyanisole (Tenox, preservative) | 0.05 | 0.05 |
| Propylene glycol dicaprylate/tricaprate (Miglyol 840, emollient) | 6 | 6 |
| Dimethicone (Silicone 225 Fluid, emollient) | 2 | 2 |
| Isopropyl myristate (IPM) (emollient) | 6 | 6 |
| Polyethylene glycol 100 stearate and glycerol monostearate (1:1) (Arlacel 165, emulsifier) | 8 | 8 |
| Polyethylene glycol 20 stearyl ether (Brij 78, emulsifier) | 1.5 | 1.5 |
| Blend IV | | |
| d-Panthenol (skin conditioner) | 2 | 2 |
| Methyl and methylchloroisothiazolinones (Kathon CG) | 1.5 | 1.5 |
| Natural soluble collagen | 1 | 1 |
| Conjugated Glycopeptide (Revitalin P) | 3 | 3 |
| Hydrolyzed animal protein (Crotein CAA) | 0.1 | 0.1 |
| Serum Proteins (Plasmatic ext. SH$_2$) | 2.5 | 2.5 |
| Yeast Extract (Yeastolan) | 3 | 3 |
| Troxerutin (moisturizer, sunscreen) | 0.5 | 0.5 |
| Blend V | | |
| Eucalyptus oil | 0.3 | — |

-continued

| Ingredient | Parts by Weight Example No. | |
|---|---|---|
| | 4 | 5 |
| Polysorbate 20 (Tween 20) | 0.1 | — |

Aqueous Blend I was prepared by mixing the ingredients in the deionized water. Blend II (prepared by simple mixing of ingredients) was then mixed with Blend I. The combined Blend I-II was then heated to 80° C.

Blend III was formed by simple mixing of the ingredients in a separate vessel while heating at 80° C.

Blend III (heated at 80° C.) was then added to the combined Blend I-II (also at 80° C.) with sweep mixing.

The combined Blend I-II-III was heated at 80° C. for 30 minutes, allowed to air cool to 60° C. and then Blends IV and V (each prepared by simple mixing) were separately added with sweep mixing.

The resulting batch was then allowed to air cool to 35° C. to form the moisturizer formulation of the invention.

EXAMPLE 6

A protective daytime lotion/moisturizer having the following composition is prepared as described below.

| Ingredient | Parts by Weight |
|---|---|
| Mix A | |
| Deionized water (diluent) | 74 |
| Magnesium aluminum silicate (thickener stabilizer) | 0.5 |
| dl-Panthenol (skin protecting agent) | 1 |
| Mix B | |
| Troxerutin | 1 |
| Octyl dimethyl p-aminobenzoic acid (sunscreen) | 2 |
| Diisopropyl dimerate (emollient oil) | 4 |
| Propylene glycol dicaprylate/dicaprate (emollient oil) | 8 |
| Propyl paraben (preservative) | 0.1 |
| Stearic acid (opacifier, bodying agent) | 2 |
| Brij 78 (Steareth 20) (emulsifier) | 2 |
| Glyceryl stearate and PEG 100 stearate (emulsifier, thickener) | 2 |
| Mix C | |
| Carbowax 400 (PEG 8) (humectant) | 2 |
| Xanthan gum (thickener, stabilizer) | 0.3 |
| Methyl paraben (preservative) | 0.2 |
| Mix D | |
| Glydant (dimethyldimethoyl hydantoin) (preservative) | 0.4 |

Each of Mixes A and B are heated to 75° C. and Mix B was added to Mix A with propeller type mixing while maintaining the 75° C. temperature for 1 hour. The resulting mixture is cooled to 65° C. and Mix C is added. The mixture is then cooled to 50° C. and Mix D is added. Cooling is continued to 30° C. to form the protective daytime lotion/moisturizer of the invention which is found to have improved feel and barrier properties, is naturally compatible with the skin and has improved skin penetrability.

EXAMPLE 7

A soothing facial make-up having the following composition is prepared as described below.

| Ingredient | Parts by Weight |
|---|---|
| Phase A | |
| Deionized water | 48 |
| Veegum R (magnesium aluminum silicate) (thickener) | 1 |
| Phase B | |
| Kaolin 2749 (skin protectant) | 4 |
| Umber 1985R | 0.5 |
| Russet C33-2527 | 0.3 |
| Yellow 2576 | 1 |
| Blue 3516 | 0.01 |
| Phase C | |
| TiO$_2$ water dispersable (90% TiO$_2$, 10% Talc) | 10 |
| Phase D | |
| Alcolec 413S (lecithin and Polysorbate 20 and sorbitan laurate and propylene glycol stearate and propylene glycol laurate) | 1 |
| Phase E | |
| Deionized water | 1 |
| dl-Panthenol (skin protectant) | 0.5 |
| Phase F | |
| Carbowax 400 (humectant) | 4.5 |
| Tegosept P (propyl paraben) (preservatives) | 0.2 |
| Keltrol F (xanthan gum) (thickener) | 0.2 |
| Phase G | |
| Deionized water | 2 |
| Triethanolamine (96%) (emulsifier) | 1 |
| Phase H | |
| Tegosept P (propyl paraben) (preservative) | 0.1 |
| Butoben (butyl paraben) (preservative) | 0.1 |
| Klearol (mineral oil) (emollient) | 5 |
| Miglyol 840 (propylene glycol dicaprylate/tricaprate) (emollient) | 6 |
| Stearic acid (emulsifier, thickener) | 3.5 |
| Tegin 515 (glyceryl monostearate) (auxiliary emulsifier, thickener) | 2.5 |
| Escalol 507 (octyl dimethyl p-amino benzoic acid) (sunscreen) | 2.5 |
| Uvinol M-40 (benzophenone 3) (sunscreen) | 0.5 |
| Troxerutin | 1 |
| Silicone 225 (emollient) | 1.5 |
| Avocado oil (emollient) | 0.5 |
| PEG-6000 distearate (emulsifier thickener) | 0.2 |
| Vitamin E, dl alpha-tocopherol (antioxidant) | 0.1 |
| Phase I | |
| Deionized water | 0.75 |
| Germall 115 (preservative) | 0.25 |
| Phase J | |
| Carbowax 400 (humectant) | 0.5 |
| Exaltolide (pentadecalactone) (odor masking agent) | 0.5 |

The Phase A ingredients are homomixed for 15 minutes. Thereafter, a mix of the Phase B ingredients are added to the Phase A mixture with mixing for 1 hour.

Phase C is then mixed with Phase AB for ½ hour under slow speed mixing. Phase D is then added to the aforementioned mix with mixing for ½ hour. Phase E is then added and thereafter Phase F is sweep mixed therein for 15 minutes. The so-formed mix is then heated to 75° C. While maintaining the mix at 75° C., Phase G is added. Phase H, heated at 80° C., is then added to the above mix with fast mixing to form an emulsion. The mix is then mixed with moderate speed, cooled to 50° C. and then combined with Phase I and mixed for 5 minutes. Thereafter Phase J is added and the mixture is cooled to 30° C. to form the make-up of the invention. The so-formed make-up of the invention is found to be soothing and noncomedongenic.

EXAMPLE 8

Cosmetic Formulation

A cosmetic formulation in the form of a facial makeup having the following composition is prepared as described below.

| Ingredient | Grams |
| --- | --- |
| Deionized water | 76 |
| Glycerin | 3 |
| 2-Pyrrolidone-5-carboxylic acid (PCA) | 0.6 |
| Methyl paraben | 0.2 |
| Ceraphyl 368 (octyl palmitate) | 5 |
| Silicone 225 (dimethicone) | 2 |
| Tween 60 (Polysorbate 60) | 3 |
| Propyl paraben | 0.1 |
| Tegin 515 (glyceryl monostearate 40% mono) | 2 |
| Promulgen D (cetearyl alcohol + ceteareth 20) | 5.5 |
| Deionized water | 0.5 |
| Dowicil 200 (Quaternium 15) | 0.1 |
| Troxerutin | 0.5 |

Glycerin, 2-pyrrolidone-5-carboxylic acid and methyl paraben are heated together to 70° to 75° C. with propeller mixing to form a first mix.

Octyl palmitate, dimethicone, polysorbate 60, propyl paraben, glyceryl monostearate and Promulgen D (cetearyl alcohol and Cetearth 20) are heated together to 70° to 75° C. with propeller mixing to form a second mix.

The second mix is then added to the first mix with propeller mixing and the mixture is then cooled to 60° C. while sweep mixing. Thereafter, aqueous Dowicil 20 (Quaternium 15) and troxerutin are added at 50° C. and the mixture is cooled to 30° C. to form the cosmetic of the invention.

EXAMPLE 9

Shampoo Formulation

A shampoo having the following composition is prepared as described below.

| Ingredient | Grams |
| --- | --- |
| Deionized water | 33 |
| Standapol ES2 (25% sodium laureth 2-sulfate) | 50 |
| Glydant (55% solution dimethyl dimethoyl hydantoin) | 0.3 |
| Standapol AB 45% (45% lauryl betaine) | 13 |
| Perfume oil | 0.5 |
| Triton X102 (octoxyonol 13) | 1 |
| Methyl paraben | 0.1 |
| FDC Yellow 6 (0.1% solution) | 0.05 |
| FDC Red 4 (0.1% solution) | 0.05 |
| 85% Phosphoric acid | (qs to pH 6.0) |
| Troxerutin | 1 |

A first mix is formed by sweep mixing deionized water, Standapol ES2, Glydant and Standapol AB 45% while heating to 60°-65° C. The first mix is cooled to 50° C. and then perfume oil, Triton X102, Tegin and the FD&C colors are added to the first mix with sweep mixing to form a second mix. The pH of the second mix is adjusted to 6.0 with phosphoric acid, at 50° C. and then the troxerutin is added at 50° C. and the mix is cooled to 30° C. to form the shampoo formulation of the invention.

EXAMPLE 10

Hair Conditioner

A hair conditioner having the following composition is prepared as described below.

| Ingredient | Grams |
| --- | --- |
| Deionized water | 90.45 |
| Genamin DSAC (Quaternium 5) | 2 |
| Potassium chloride | 0.15 |
| Methyl paraben | 0.2 |
| Propyl paraben | 0.1 |
| Hostacerin T-3 (Ceteareth 3) | 1.5 |
| Cetyl alcohol | 1.5 |
| Stearyl alcohol | 1.5 |
| Perfume oil | 0.1 |
| Triton X102 (octoxyonol 13, that is, polyoxyethylene (13) octyl phenyl ether) | 0.5 |
| Troxerutin | 0.5 |

The Genamin DSAC, KCl, Tegin, troxerutin and water are mixed together and heated at 70°-75° C. with propeller mixing to form a first mix.

The Hostacerin T-3, cetyl alcohol and stearyl alcohol are mixed together at 70°-75° C. with propeller mixing to form a second mix.

The second mix is added to the first mix with propeller mixing. The combined mix is subjected to sweep mixing at 50° C. and perfume oil and Triton X102 are added. The batch is then cooled to 30° C. to form the hair conditioner of the invention.

What is claimed is:

1. In an improved sunscreen or sunblock composition comprising from about 50 to about 90% by weight water, from about 1 to about 20% by weight of at least one emollient, from about 1 to about 10% by weight of at least one emulsifier, from about 0.05 to about 2% by weight of at least one preservative and wherein the improvement comprises including a tri(hydroxyalkyl)-rutoside in an amount within the range of from about 0.2 to about 3% by weight based on the total composition to impart moisturizing properties to said composition and enhance sunscreening properties thereof.

2. The composition as defined in claim 1 wherein said tri(hydroxyalkyl)rutoside is troxerutin.

3. The composition as defined in claim 1 in the form of a moisturizing sun screen composition and includes from about 1 to about 15% by weight of at least one UV-B ultraviolet absorbing agent.

4. The composition as defined in claim 3 wherein said UV-B ultraviolet absorbing acid is 4-(dimethylamino)-benzoic acid, 2-ethyl hexyl ester.

5. The composition as defined in claim 1 further including one or more UV-A absorbing and one or more UV-B absorbing agents.

6. The composition as defined in claim 5 wherein the UV-A absorbing agent or agents are present at from about 0.5% to about 10% by weight and the UV-B absorbing agent or agents are present at from about 3% to about 10% by weight.

7. The composition as defined in claim 6 wherein the UV-A absorbing agent is one or more selected from the group consisting of 2-(2'-hydroxy-5'-methylphenyl)benzotriazole; 2-(2'-hydroxy-5'-t-octylphenyl)benzotriazole; 2,4-dihydroxybenzophenone; 2-hydroxy-4- methoxybenzophenone; 2,2', 4,4'-tetrahydroxybenzophenone; 2,2'-dihydroxy-4,4'-dimethoxybenzophenone; 2,2'-dihydroxy-4-methoxybenzophenone; 2-ethylhexyl-4-phenylbenzophenone carbonate; 2-hydroxy-4-methoxy-4'-methylbenzophenone; 2-hydroxy-4-(n-octyloxy)benzophenone; butyl methoxydibenzoyl methane; benzphthalide; 4-phenylbenzophenone; and 2-ethylhexyl-2-cyano-3,3'-diphenylacrylate and the UV-B absorbing agent is one or more selected from the group consisting of 4-(dimethylamino)benzoic acid, ethyl ester; 4-(dimethylamino)benzoic acid, 2-ethylhexyl ester; 4-(dimethylamino)benzoic acid, pentyl ester; glyceryl p-aminobenzoate; isobutyl p-aminobenzoate; 2-ethylhexyl methoxy cinnamate; phenylbenzimidazole sulfonic acid; homomenthyl salicylate, ethyl hexyl salicylate and isopropyl p-aminobenzoate.

8. The composition as defined in claim 6 wherein the UV-A absorbing agent is 2-hydroxy-4-methoxybenzophenone alone or in combination with 2,2'-dihydroxy-4-methoxybenzophenone and the UV-B absorbing agent is 4-(dimethylamino)benzoic acid, 2-ethylhexyl ester.

9. The composition as defined in claim 4 wherein the tri(hydroxyalkyl)rutoside is present in an amount within the range of from about 0.3 to about 3% by weight.

10. The composition as defined in claim 9 wherein the tri(hydroxyalkyl)rutoside is troxerutin.

11. The composition as defined in claim 1 wherein water is present in an amount of from about 50 to about 90% by weight, emollients are present in an amount of from about 1 to about 5% by weight, emulsifiers are present in an amount of from about 1 to about 10% by weight, thickeners are present in an amount of from about 0.1 to about 1% by weight, humectants are present in an amount of from about 1 to about 5% by weight, preservatives are present in an amount of from about 0.5 to about 1% by weight.

12. The composition as defined in claim 4 offering maximum ultraviolet protection comprising from about 60% to about 80% by weight of water, from about 0.5 to 2% by weight of troxerutin, from about 0% to about 5% by weight of 2-hydroxy-4-methoxybenzophenone alone or in combination with 2,2'-dihydroxy-4-methoxybenzophenone, from about 2% to about 10% by weight of 4-(dimethylamino)benzoic acid, 2-ethylhexyl ester, from about 1% to about 5% by weight of emollients, from about 1% to about 10% by weight of emulsifiers, and up to about 1% by weight of combined preservatives, antioxidants and fragrances.

13. The composition of claim 12 comprising about 73% by weight of deionized water, about 2% to about 4% by weight of 2-hydroxy-4-methoxy-benzophenone, up to about 1% by weight of 2,2'-dihydroxy-4-methoxybenzophenone, about 3 to 5% by weight of 4-(dimethylamino)benzoic acid, 2-ethylhexyl ester, from about 2% to about 4% by weight of emollients, from about 3% to about 8% by weight of emulsifiers, and up to about 1% by weight of combined preservatives, antioxidants and fragrances.

14. In a method of enhancing the sunscreen properties of a sunscreen composition which contains from about 2 to about 15% by weight of one or more ultraviolet absorbing agents, the improvement which comprises including at least about 0.5% by weight of troxerutin within the composition.

15. The method as defined in claim 14 wherein the sun screen composition contains from about 3% to about 15% by weight of ultraviolet absorbing agents by weight of the composition.

16. The composition as defined in claim 1 wherein said tri(hydroxyalkyl) rutoside is troxerutin and said sunscreen agent is 4-(dimethylamino)benzoic acid, 2-ethylhexyl ester, wherein the troxerutin is present in a weight ratio to the 2-ethyl hexyl ester of within the range of from about 0.04:1 to about 3:1.

17. The composition as defined in claim 16 wherein the troxerutin is present in a weight ratio to the 4-(dimethylamino)benzoic acid, 2-ethylhexyl ester of within the range of from about 0.1:1 to about 2:1.

18. The composition as defined in claim 1 further including a thickener in an amount within the range of from about 0.05 to about 1% by weight.

* * * * *